United States Patent [19]

Hill

[11] Patent Number: 5,413,127
[45] Date of Patent: May 9, 1995

[54] DENTAL FLOSS OR TAPE

[75] Inventor: David M. Hill, Big Mill Leek, United Kingdom

[73] Assignee: Jordan A/S, Norway

[21] Appl. No.: 242,709

[22] PCT Filed: Feb. 13, 1991

[86] PCT No.: PCT/GB91/00213
  § 371 Date: Aug. 12, 1992
  § 102(e) Date: Aug. 12, 1992

[87] PCT Pub. No.: WO91/11970
  PCT Pub. Date: Aug. 22, 1991

Related U.S. Application Data

[63] Continuation of Ser. No. 920,552, Aug. 12, 1992, abandoned.

[30] Foreign Application Priority Data

Feb. 14, 1990 [GB] United Kingdom ............... 9003292

[51] Int. Cl.$^6$ ............................................. A61D 5/00
[52] U.S. Cl. ............................................. 132/321
[58] Field of Search ........................... 132/321, 329

[56] References Cited

U.S. PATENT DOCUMENTS

| | | | |
|---|---|---|---|
| 3,838,702 | 10/1974 | Standish | 132/89 |
| 3,943,949 | 3/1976 | Ashton et al. | 132/89 |
| 4,029,113 | 6/1977 | Guyton | 132/91 |
| 4,776,358 | 10/1988 | Lorch | 132/321 |
| 4,836,226 | 6/1989 | Wolak | 132/321 |
| 4,996,056 | 2/1991 | Blass | 132/321 |
| 5,033,488 | 7/1991 | Curtis et al. | 132/321 |

FOREIGN PATENT DOCUMENTS

| | | |
|---|---|---|
| 0080440 | 6/1983 | European Pat. Off. |
| 0136727 | 4/1985 | European Pat. Off. |
| 0172671 | 2/1986 | European Pat. Off. |
| 0335466 | 10/1989 | European Pat. Off. |
| 0423541 | 4/1991 | European Pat. Off. |
| 1380032 | 1/1975 | United Kingdom |
| 2216803 | 10/1989 | United Kingdom |
| 2258402 | 2/1993 | United Kingdom |

Primary Examiner—Cary E. O'Connor
Attorney, Agent, or Firm—W. Thad Adams, III

[57] ABSTRACT

A dental floss or tape has a multifilament polyamide core and a continuous PTFE coating applied by passing the core through an aqueous PTFE dispersion and heating the deposited particles such that they coalesce into a layer without substantially effecting the structure of the core.

9 Claims, 1 Drawing Sheet

DENTAL FLOSS OR TAPE

This application is a continuation of application Ser. No. 07/920,552, filed Aug. 12, 1992, now abandoned.

This application is a PCT application. This application claims the priority date of Feb. 14, 1990 for Great Britain Patent Application No. 9003292.1.

The present invention relates to dental floss or tape.

Dental floss or tape is usually a multi-filament, possibly continuous strand, material such as polyamide or polyester. Its elements are drawn and twisted to improve strength and resilience.

It is already known that dental floss or tape may be coated with a wax based coating using polyethylglycol (PEG) or hot wax. Furthermore it is not unusual to add flavouring flouride and/or abrasive to the floss or tape. Such flosses are disclosed, for example, in U.S. Pat. Nos. 3,838,702, 3,943,949 and 4,029,113. Un-waxed dental floss or tape is also available using an acrylic emulsion coating to seal and/or bind the floss or tape.

Prior flosses have not been found to be completely satisfactory by the user as the wax coating is usually scraped off when the floss is being used to clean interdental spaces depositing the wax on the teeth which thereafter feel sticky. Additionally the removal of the wax leads to an increased co-efficient of friction between the floss and teeth and gums and this, coupled to the deterioration of the floss when its wax binding coat is removed, means that the floss rapidly disintegrates and often breaks, rendering it useless, troublesome and annoying.

It has been proposed in the past to decrease the co-efficient of friction by incorporating powdered polytetrafluoroethylene (PTFE) in the wax binder, such a solution having been proposed in European Patent Application No. 0358363A but this proposal still suffers from the disadvantage of removal of the coating during use and the subsequent possible disintegration and destruction of the floss.

Prior patents, for example, European Patent Application 0335466A and U.S. Pat. No. 477,635A have recognized that PTFE has a relatively high tensile strength and will give the feature of reduced co-efficient of friction without the disadvantage of subsequent possible destruction if it is used in place of the polyamide or polyester formerly employed as the core of the floss or tape. Unfortunately, PTFE is a relatively expensive material, for example, it is six times more expensive than polyamide and consequently the considerable disadvantage of this proposal, bearing in mind that the product is a "throw away" product, is the high cost. A similar disadvantage is displayed in U.S. Pat. No. 4,836,226 which discloses the use of a PTFE coating on an elastic material which is used while in a stretched condition. In this proposal the elastic material and PTFE have widely differing moduli of elasticity so that stretching the core will disrupt the PTFE coating.

It is an object of the present invention to obviate or mitigate these and other disadvantages.

According to the present invention there is provided a method of producing a fluorocarbon coated dental floss or tape comprising passing spun filamentary elements forming a multi-filament core through a dispersion including fluorocarbon particulate material such that fluorocarbon particles are deposited upon the multi-filament core and heating the deposited fluorocarbon particles such that they coalesce into a fluorocarbon coating on the core.

Preferably prior to passing the core through the dispersion its filaments are twisted.

Preferably the core is heated to evaporate the liquid component of the fluorocarbon dispersion and further heated to coalesce the fluorocarbon upon the core, preferably into a continuous layer.

Preferably a wax layer including any one or more of the group comprising flavouring fluoride, and abrasive is added to the core after the fluorocarbon coating is applied.

Preferably prior to passing the core through the fluorocarbon dispersion the core is dyed.

Preferably the fluorocarbon particles deposited on the core are subjected to a temperature within the range 355° F. to 400° C., for a short period to ensure the core does not melt appreciably as the particles coalesce into a continuous coating on the core.

Desirably the fluorocarbon particles deposited on the core are subjected to an upper temperature of 360° C. as the core passes the heating means at a speed of m/min.

Further according to the present invention there is provided a dental floss or tape comprising a core of filamentary material and a fluorocarbon coating formed from coalesced fluorocarbon particles.

Preferably the fluorocarbon is polytetrafluoroethylene (PTFE),

Preferably, the coating is arranged to ingress within the core and is formed by polytetrafluoroethylene particles coalesced into a continuous layer.

Preferably, a wax layer is added to the fluorocarbon coating.

Preferably, the filaments are twisted prior to application of the fluorocarbon coating.

Preferably the filaments are polyamide or polyester.

An embodiment of the present invention will now be described by way of example only with reference to the accompanying drawings in which.

Figure 1:
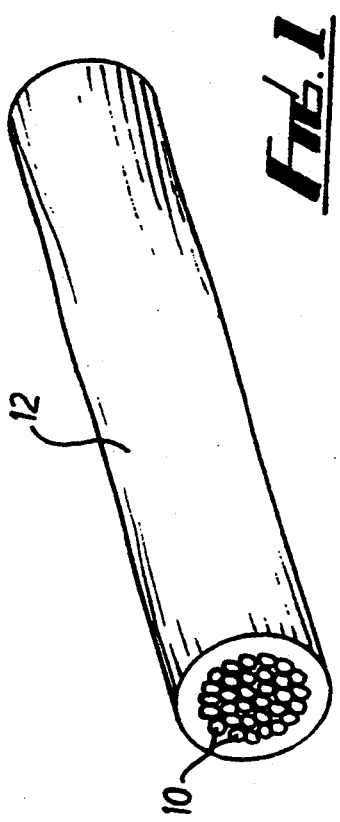
FIG. 1 illustrates a length of coated floss.
Figure 2:
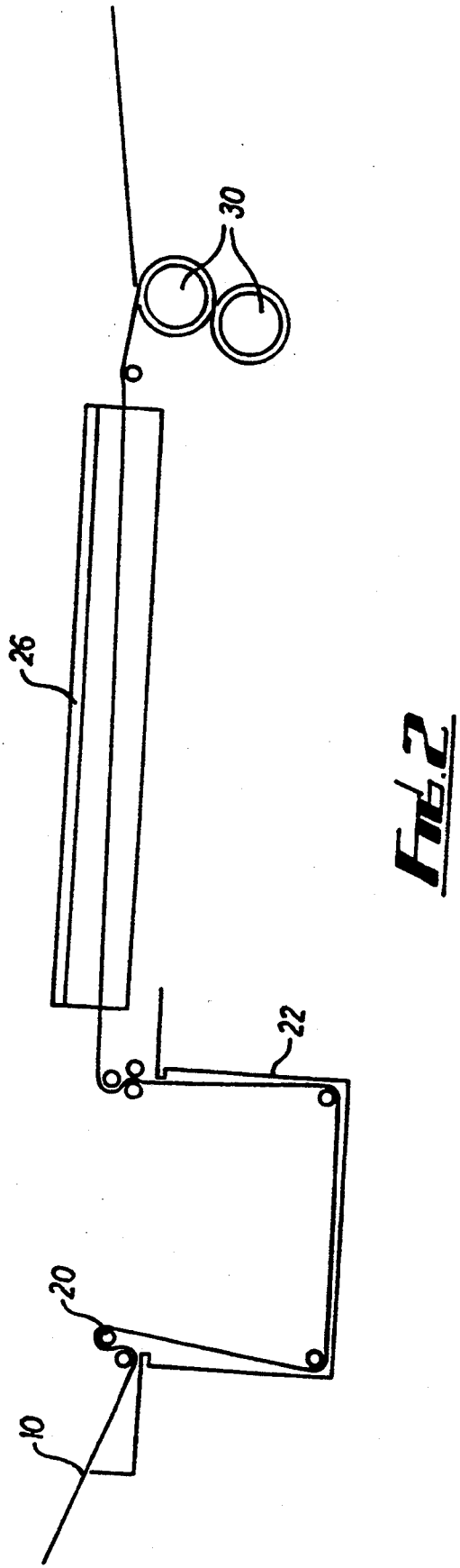
FIG. 2 shows diagrammatically apparatus for coating floss.

It is usual to take thirty two filaments of extruded and stranded material to form a dental floss core 10. These filaments are formed of polyamide or polyester material and are usually continuous extruded strands. It will be appreciated that the type of filament and its dimensions will be chosen in accordance with requirements, however, it is not unusual to use 940 denier materials with thirty-two filaments in a core 10 or, as an alternative, thirty two minicores each comprising eight filaments of 100 denier. The floss core 10 is twisted and if it is necessary to dye the floss or tape it is at this stage that dying takes place.

Once twisted the core is normally stored on creels until required for further processing. During further processing the floss 10, after passing through pre-tensioning bars 20 is drawn through a tank 22 containing a dispersion of PTFE in water and a non-ionic wetting agent as stabiliser. This dispertion adheres itself to the core 10 and ingresion of dispersion into the filaments of the core can be facilitated through agitation and other means (not shown). Once the core 10 has been drawn through the tank 22 of PTFE dispersion it passes over tension rollers 24 which further ensure that PTFE particles and their carrier are impregnated into the core. The core and its coating 12 of PTFE particles from the dispersion is then passed through an oven assembly 26 which is some 10 m in length.

On passage through the tension rollers 24 excess dispersion is squeezed from the core and, as mentioned above pressed into the interstices between the filaments of the core. In the first section of the oven, which is of approximately 2 m length the water carrier is evaporated off leaving behind the PTFE particles which, at this stage, are only mechanically adhered to the core 10.

During subsequent passage through the oven, that is the approximate remaining 8 m, heat applied by the infra-red heaters within the oven will cause the PTFE particles to coalesce into what is desireably a continuous unbroken coating but may be a coating of coalesced particles which, if not completely continuous longitudinally and circumferentially, has continuity by way of unbroken areas of coalesced particles of practical length.

By a balance of the speed of the core through the oven and the temperature therein it is possible to coalesce or sinter the particles onto the polyamide core without causing permanent unacceptable damage to the core, which has a melting point lower than the coalescing or sintering temperature of the particles.

In the example illustrated in the drawing, up to a hundred cores are treated simultaneously and they are caused to pass through the ovens at a speed of between 30 and 60 m/min, preferably 40 m/min. At this speed the temperatures in the oven, which is arranged in four parts are: part 1 355° C., part 2 375° C., part 3 90° C., and part 4 400° C. Part 1 forms the first section referred to above and parts 3, 4; which total some 8 mm length from the second oven section.

A typical PTFE dispersion has the following specification:

Composition: PTFE particles, water, non-ionic wetting agent.
  solids content (% PTFE by weight) 58.5%
  particle size, average diameter 0.23 Um
  resin dry weight (58.5% solids) 870 g/1
  specific gravity of dispersion (58% PTFE) 1.49
  specific gravity of sintered resin 2.23

The dispersion can be diluted from the values set out in the table above by adding water up to the ratio of 1:1.

After passing through the oven 26 the PTFE coated core passes around a pair of tension rollers 30 by way of a drop wire device 28 and may be stored on creels (not shown) or passed through a further coating stage.

Various coatings such as wax or an acrylic emulsion can be applied on top of the fluorocarbon coating. Furthermore it is conventional with dental floss or tape to apply fluoride, flavourings and abrasive to assist its function and acceptability.

Various modifications can be made without departing from the scope of the invention. The coating need not be PTFE but could be any other suitable fluorocarbon lubricant applicable in powder form in a dispersion and coalescible to give a continuous coating on the floss core.

I claim:

1. A method of producing a fluorocarbon-coated dental floss or tape comprising the step of coating a multi-filament core with a pure, substantially continuous outer layer of coalesced fluorocarbon particles bound to each other on the core for permanently adhering to the core during use of said dental floss or tape.

2. A method of producing a fluorocarbon-coated dental floss or tape comprising the steps of:
    (a) depositing fluorocarbon particles entrained in a fluorocarbon dispersion upon the surface of a multi-filament core;
    (b) heating the core to evaporate a liquid component of the fluorocarbon dispersion; and
    (c) sintering the core such that the fluorocarbon particles coalesce and bind to each other to form a pure, substantially continuous fluorocarbon coating on the core for permanently adhering to the core during use of said dental floss or tape.

3. A method according to claims 2, comprising the further step of twisting the filaments of said multi-filament core prior to passing the core through the fluorocarbon dispersion.

4. A method according to claim 2, comprising the further step of adding a wax layer to the fluorocarbon-coated core, said wax layer including at least one of the group consisting of flavoring fluoride and abrasive.

5. A method according to claim 2, comprising the further step of dying the multi-filament core prior to passing the core through the fluorocarbon dispersion.

6. A method according to claim 2, wherein the sintering step comprises the step of subjecting the fluorocarbon particles deposited on the core to a temperature within the range of 355° F. to 400° C. for a short period to ensure that the core does not melt appreciably as the particles coalesce into a pure, substantially continuous coating on the core.

7. A method according to claim 2, wherein the heating step comprises the step of subjecting the fluorocarbon particles deposited on the core to an upper temperature of 360° C. as the core passes heating means at a speed of between 30 and 60 m/min.

8. A dental floss or tape comprising:
    (a) a core of filamentary, dental floss or tape material; and
    (b) a pure, substantially continuous fluorocarbon coating formed on an outer surface of said core for lubricating said dental floss or tape, said coating being formed of coalesced fluorocarbon particles bound to each other for permanently adhering to the core during use of said dental floss or tape.

9. A floss or tape according to claim 8, wherein the coalesced fluorocarbon particles of said fluorocarbon coating comprise polytetrafluorethylene particles.

* * * * *